United States Patent [19]

Schlawne

[11] Patent Number: 4,817,431

[45] Date of Patent: Apr. 4, 1989

[54] DEFECT DETECTION IN CYLINDRICAL OBJECTS

[75] Inventor: Friedhelm Schlawne, Kerpen-Sindorf, Fed. Rep. of Germany

[73] Assignee: Mannesmann AG, Duesseldorf, Fed. Rep. of Germany

[21] Appl. No.: 69,417

[22] Filed: Jul. 1, 1987

[30] Foreign Application Priority Data

Jul. 3, 1986 [DE] Fed. Rep. of Germany ....... 3622500

[51] Int. Cl.$^4$ ........................................... G01N 29/04
[52] U.S. Cl. ..................................................... 73/600
[58] Field of Search ................ 73/622, 637, 638, 632, 73/600, 618

[56] References Cited

U.S. PATENT DOCUMENTS 3,930,404 1/1976 Ryden, Jr. ............................ 73/622
4,651,568 3/1987 Reich et al. ........................... 73/622

Primary Examiner—Stewart J. Levy
Assistant Examiner—Lawrence G. Fess
Attorney, Agent, or Firm—Ralf H. Siegemund

[57] ABSTRACT

Defects are detected in cylindrical rods, tubes or the like by a stationary transmission and receiving device arranged along the path which the test object passes axially by providing per test cycle a particular pulse being split for propagating bidirectionally azimuthally in the test object; both pulses are received repeatedly, once per circulation, so that a plurality of pulses appear with gradually declining amplitude; a sequence of burst signals, each of limited duration, is provided for purposes of timing and gating the burst being repeated per circulation on the basis of the expected and known propagation time between transmission and receiving portions; peaks of the received signal are detected once or twice per circulation and in synchronism with the timing and gating signal; the respective detected peak signals are digitized, summed in groups and the quotient of the sums is formed as quality indicator.

2 Claims, 3 Drawing Sheets

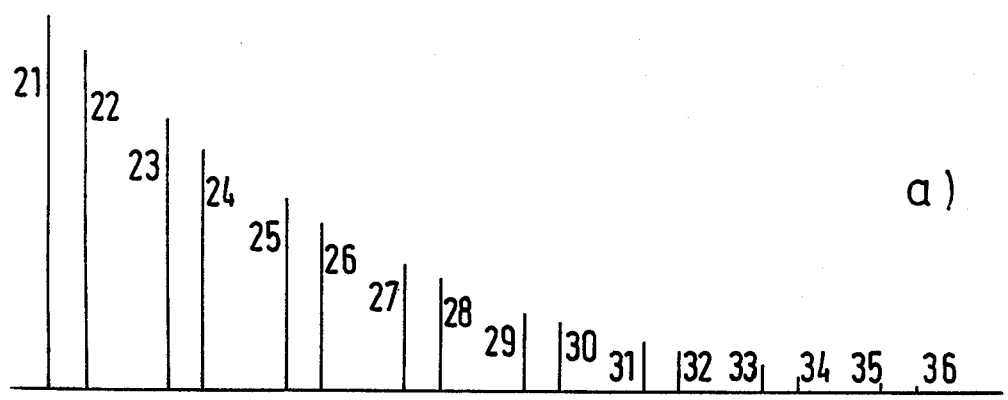
a)
b)
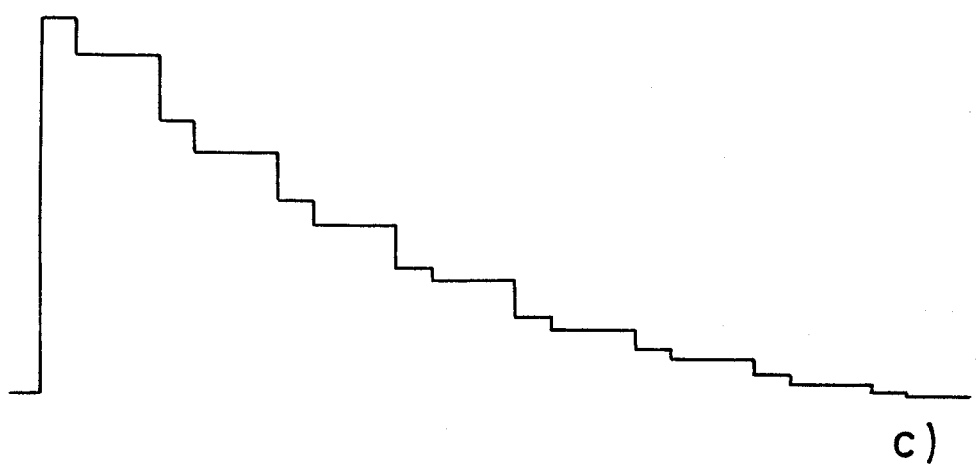
c)
Fig.2

DEFECT DETECTION IN CYLINDRICAL OBJECTS

BACKGROUND OF THE INVENTION

The present invention relates to ascertaining defects in cylindrical objects such as tubes or pipes. More particularly, the invention relates to the testing of tubes, pipes or rods without rotating them but passing them past stationary transmitting and receiving equipment whereby tangentially produced azimuthal wave pulses are produced at a certain rate and received and the amplitudes are processed under formation of quotients for determining defects in the test object.

German printed patent application No. 26 05 405 discloses and suggests a method and equipment of the general type and variety to which the invention pertains and constituting the point of departure for further development. These kinds of equipment and types of methods are advantageous whereby specifically electrodynamic transducers are used for converting ultrasonic energy into electrical pulses and vice versa. These transducers will be arranged vis-a-vis the test object. The electrodynamic operation does not require any liquid coupling as is necessary in case of ultrasonic transducers. Also the rotation of the test object or of the equipment is to be avoided which is, from an equipment point of view, an advantage. However, it was found that this mode of processing the signals produced and generated by and in the equipment as well as by the test object are not reliable. It is to be observed that the ends (axial) of the test object do produce certain parasitic reflections and interferences which has some influence on the signals as they are received. These parasitic signals do not drop off in a monotonic function and are, therefore, no reliable indicator for the quality of the test object. Moreover, quotient formation of two amplitude maximum values as processed is rather sensitive against statistic interferences. On the other hand a complete digitalization of any and all signals as received and a search for individual amplitude maxima and subsequent evaluations thereof are too time consuming.

DESCRIPTION OF THE INVENTION

It is an object of the present invention to increase the speed of the test method of the type to which the invention pertains as outlined above, and to increase the reliability of test signal processing and evaluation as to defect detection.

It is a particular object of the invention to detect defects in cylindrical objects, hollow or solid ones, by means of stationary equipment which produces in the test object ultrasonic waves that progagate azimuthally and circulate in that fashion under gradual decay.

In accordance with the preferred embodiment of the present invention, it is suggested to provide burst signals for synchronizing the detection of the signals to the circulation period; to provide peak detection during limited periods, to sum early and late received peaks separately and to form a quotient.

Through the synchronous production of burst signals one can dispense with the digitilization of the entire signal train as received by a pick up circuit. The amplitude max is detected through the generation of a burst signal serving as a time gating reference signal. Per circulatory period only one digital (peak) value is actually produced corresponding to whatever maximum value occurs within a limited gating period. This mode of operation results in a plurality of peak value signals per test cycle. A detailed evaluation of sequences of these peaks as received will be carried out through groupings and processings of groups of pulses, in that the sum of earlier peaks within a cycle period are provided, and the sum of later peaks, definite in number, is separately provided; the quotient of these sums is formed, and the quotient indicates the particular quality for the rod or tube. This quotient should be quite constant in sequential test cycles in the absence of defects representing a regular amplitude decline. Defects may provide e.g. rapid scattering decay on multiple circulations.

DESCRIPTION OF THE DRAWINGS

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings in which:

FIG. 1a is a portion of FIG. 1 with a modification;

FIGS. 2a, 2b and 2c are related diagrams of signals as produced in the circuit shown in FIG. 1.

Turning to the detailed description of the drawings, FIG. 1 illustrates the arrangement of equipment by means of which the invention can be practiced and it includes particular inventive equipment. Herein reference numeral 5 refers to a cylindrical round test object but it could be a tube or pipe. The test equipment includes, basically, a transmitter 4 and a receiver 6. The two devices 4 and 6 are electrodynamic transducers which are electrodynamically coupled to the test object 5, that is transmitter 4 does not provide but generates in test object 5 an ultrasonic signal. Analogously, arrival of an ultrasonic signal under transducer 6 produces therein an electrodynamic response. The two transducers 4 and 6 are arranged azimuthally displaced from each other in that the receiving transducer 6 is clockwise displaced from the transmitting transducer 4 by an angle that is between 90 and 180 degrees. Other angles including 180 degrees and zero degrees will be discussed as special cases below.

Figure 1:
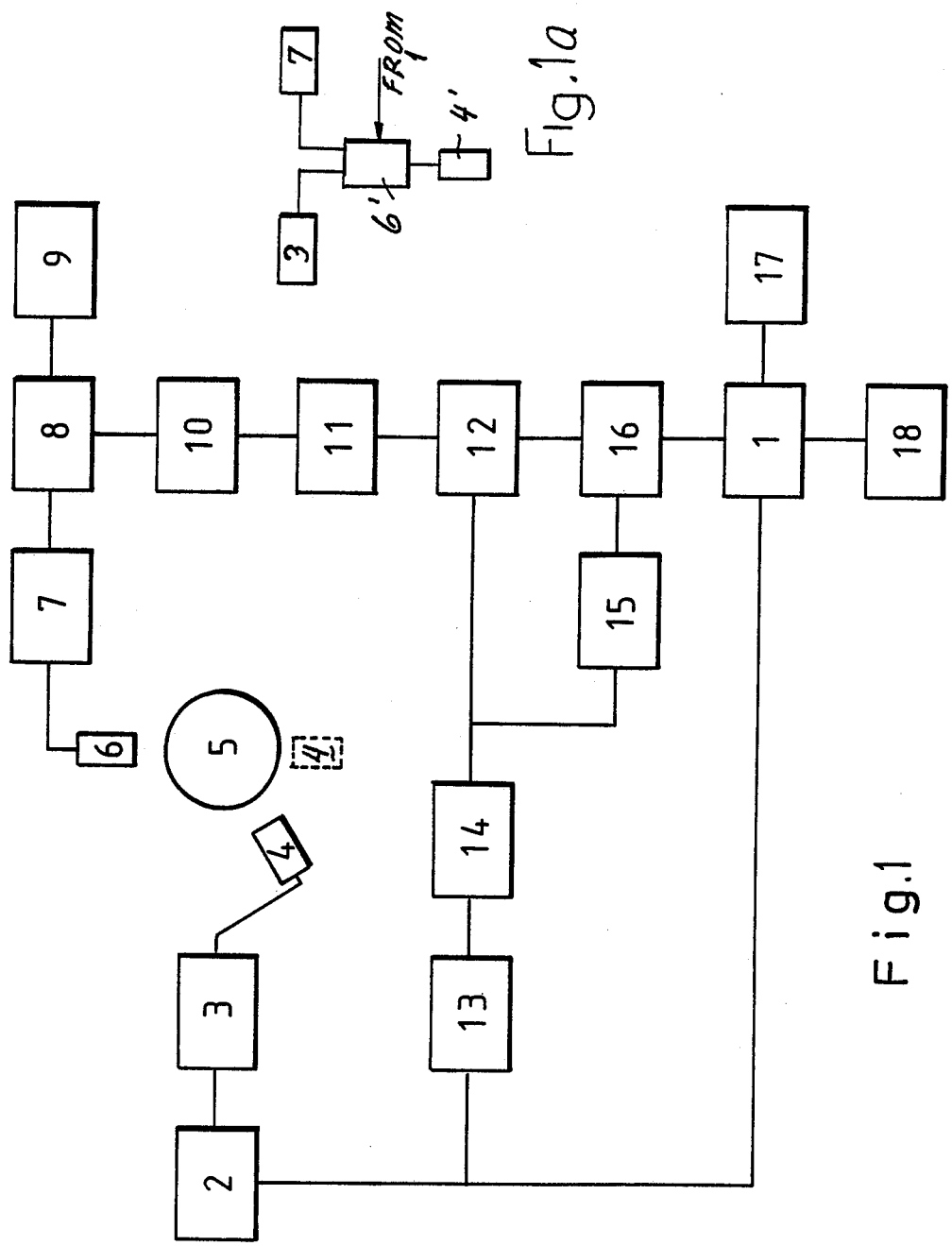
FIG. 1 is a block diagram of a general nature for demonstrating practicing the preferred embodiment of the invention in a best mode configuration.

A computer or process controller 1 with computing capability provides in the beginning of a test cycle a particular trigger signal to the source 2 which provides an electrical signal to an amplifier 3 which in turn controls the transmitter 4. The transmitter 4 produces a wave in the test object 5 which wave is split and propagates predominantly to the left an to the right from the point of production in the test object near the surface thereof.

Owing to the particular azimuthal displacement of the transducer 6 from the transmitter 4, the receiver receives first the signal which propagates counterclockwise in the test object. FIG. 2a provides a representation at 21 of such a signal. Subsequently the counterclockwise wave 22 is received by the transducer 6. The two ultrasonic waves continue to circulate respectively clockwise and counterclockwise. Further passages are indicated in FIG. 2a in pairs 23,24;25,26;27,28 etc. until only rather small signals 35 and 36 constitute, say, a last pair of detectable signals slide pair resulting from clockwise and counterclockwise transmission of signals in the test object 5.

These signals are, as stated, received by the transducer 6 and preamplified by a conventional preamp 7 with a narrow band amplification at 8. The signals so amplified may simply be displayed by a suitable monitor 9. On the other hand the amplified narrow band signal is rectified (rectifier 10), passed through a low pass filter 11 to a peak detector 12.

On the other hand the trigger signal which gave rise to all these various events is passed through a delay line 13 to another signal source 14 which produces a synchronized burst signal; the envelope (after squaring) is shown in FIG. 2b. This signal is a sequence of signals having a burst rate frequency that is precisely the circulatory frequency of an ultrasonic signal around the periphery of test object 5. This burst signal is used as a timing and gating reference signal in the detector 12. The method operating with the described apparatus uses primarily a sequence of signals (FIG. 2a or 3a) within a test cycle and having a regular rate of appearance owing to the circulation. By means of the signal source 14 a burst signal is produced, the frequency of which agrees with the peak rate frequency of a full circulation. The length of any test cycle depends on the order of magnitude of still measurable peaks as they decay after many circulations. The burst signals are gating signals appearing in synchronism with the peak. Conceivably, one takes a detected peak in each instance from detector 12 and re-synchronizes the burst signal generation to avoid phase drift. These gating signals from the specific embodiment of FIG. 1 are produced in pairs corresponding to the difference in propagation time from transmitter to receiver for clockwise and counterclock wise waves. In fact device 14 may be duplicated with dual triggering from dual outputs of delay 13 corresponding to test wave propagation difference.

A delaying cicuit 15 serves to provide in each instance a delayed trigger signal for and in an analog-to-digital converter 16. The converter 6 digitizes the output signal of the peak detector 12 as shown in FIG. 2c. Hence, the burst signals furnish brief analog signal sample periods, during the short periods of time in which circulating ultrasonic signals are expected to arrive. The detector 12 holds any peak detected during the gating period at the end of the burst signal sample period and that signal is then digitized by 16. The digital data as provided by the converter 16 is fed to the computer 1 as an input. The result is indicated for example by a marking unit 17 which provides suitable marking of the tube or rod 5 being tested, either in case it is defective or in case it is not defective. Separately a record and storage unit 18 receives the relevant error information that pertains to the particular test object 5 being tested.

Particularly simple results are obtained when one uses a single transducer 4' (see e.g. FIG. 1a) which, following a transmission and energization of a particular pulse that is being set into the test object 5, is switched over by a gating device 6' to serve as a receiver. The change over is controlled by the computer 1. Of course the received signal now results from two circularly circulating pulses, arriving at the receiver for reasons of symmetry at the same time. The peak detection principle and the principle of sequential peak detections can be used also here. In this case one may use either a transducer which is switched over from transmission to receiving and vice versa. Alternatively one can use a single transducer with two coils or coil systems—one provided for transmission and the other one for receiving.

Other simple relations obtain when the receiver 6 and the transmitter 4 are diametrically opposed on object 5 (see dash line position for transmitter 4 in FIG. 1). Again, only one pulse will result per circulation cycle since the two propagating signals arrive at the receiver always at the same time. Please note, if they do not so arrive, then there is present a certain case of anisotropy resulting in dispersion which will reflect in a different rate of decay of the amplitude sequence. In all these cases, of course, if there has occured some interference at some point, somewhere, and if the two waves encounter different interferences then one can also say that there is a defect which is reflected in a distortion of the otherwise expected regular amplitude decay of detected peak values. In any event, only one peak is detected per circulation and, as stated, the sequence decays within a test cycle. Also there is particularly a uniformly decaying sequence of peaks when the transmitter and receiver transducers are arranged at a spacing equal to half the wavelength of the predominant wave being produced. Another simple structure of the sequence of peaks is obtained in a 90 degrees shifted position of transmitter and receiver. In that case the two waves will arrive alternatingly at the receiver which means one evaluates in effect twice the number of pulses and each circulation is processed separately. This is another special case of the FIG. 1 and 2 instance.

Figure 3:
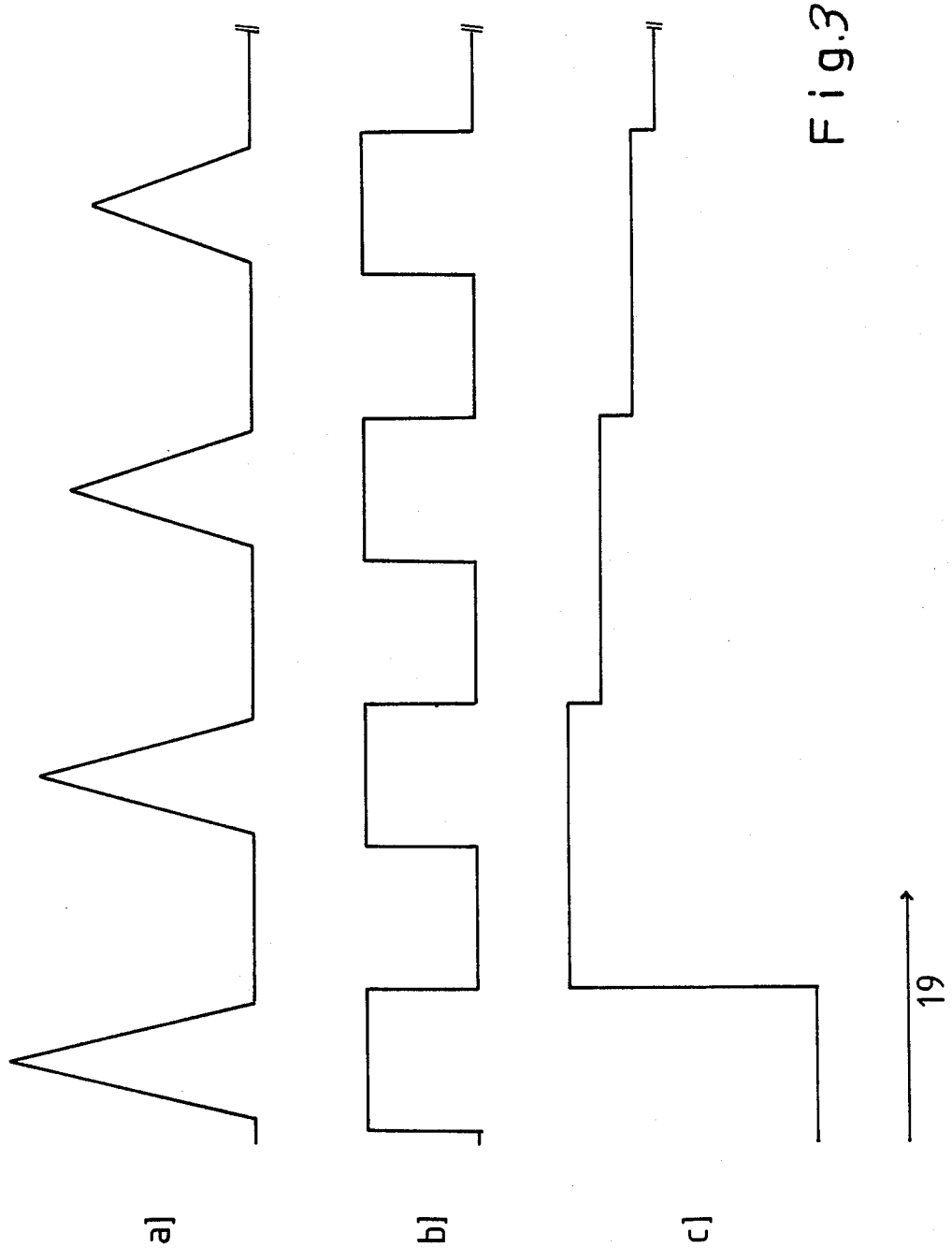
FIGS. 3a, 3b and 3c are related diagrams of signals reproduced in a simplified example of FIG. 1.

FIG. 3 illustrates again a measuring signal as received but here in the simplified case of one pulse per circulation. Thus it is assumed that there is receiver/transmitter as per FIG. 1a; alternatively the transmitter is placed in the dash line position of FIG. 1 so that the clockwise and counterclockwise signals meet at the receiver 6. FIG. 3b illustrates the burst and gating signal appropriately shifted in accordance with the expected propagation time. Coincidence is adjusted as indicated. The burst signal serves as a time gate for the peak detector 12 so that the peak detector response is limited to those periods in which the signal is to be expected. The peak detector 12 will within that limited period of time acquire and then hold the detected peak value and hold it until the signal is digitized by circuit 16. The output of that circuit 16 is as shown in FIG. 3c (in analog format). A trigger signal derived from the burst signal by means of circuit 15 and having a particular temporal relationship to the (end of the) burst signal proper is used to operate the analog to digital converter 16 to obtain the digitalization at the end of the gating period. The resulting digital signal will be fed to the computer 1 and it will be apparent that for each circulation there is a new value that is being passed to the calculator.

Generally speaking the evaluation of the measured, detected and acquired peak signals is not limited to one or two peak values. From a standpoint of quality control and reliable evaluation one will proceed as follows. At first one uses several peaks as they occur in the beginning of the peak sequence being illustrated in FIG. 2a or 3a. The summing of the first two values is sufficient but for purposes of eliminating statistical errors a large plurality of initial peaks may be summed. Two peaks are identified by way of example to be the peak values of 21 and 22. Following which the sum of the following peaks are formed. Basically one will sum peak numbers 1 through n and separately peak numbers n+1 to m where m is the number of the last peak that was recognized. For example if altogether 20 peaks are ascertained it may be advisable to sum peak 1 through 7 and to form subsequently the sum of the peaks 8 to 20 or in the case shown, the sum of peaks from 23 to 36 is formed.

Having done so one obtains two sums, and the computer 1 will now form the quotient of these two peak sums. This quotient is in fact an index or indicator for the quality of the material in the test object. The quotient is formed continuously as the object 5 moves axially i.e. one quotient per test cycle, and as the object 5 moves one test cycle after the other is being produced. Consistent quality should result in a consistent quotient value sequence. It should be noted that the entire process can be carried out very quickly which means the test object can axially advance fairly rapidly and one needs very little time in terms of process time. Just the formation of sums and quotients is needed. The delay in between sequential pulses is a measure in terms of unit time. These parameters are sufficient for the calculation. One can therefore provide a speed of operation which is no longer limited by the processing of the equipment, but the test speed is merely limited by the propagation speed of the waves and by the generation of many number of peaks. This of course depends on the relative acoustic parameters of the material being tested. Owing to the formation of the quotient any variations in coupling of the transducers is eliminated since the variations affect all of the amplitudes alike, and the contour of the peaks in relation to each other is not changed by such coupling variations. The formation of sums particularly following a number of circulation runs, also eliminates the edge effect as it is produced at the axial ends through reflections, interferences and the like.

The invention is not limited to the embodiments described above but all changes and modifications thereof, not constituting departures from the spirit and scope of the invention, are intended to be included.

I claim:

1. Method for detecting defects in a cylindrical test object having an axis, there being a stationary transmission and receiving device arranged about a path along which the said test object passes in an axial direction, comprising the steps of:

providing a plurality of test cycles and one particular pulse per test cycle by means of a transmission portion of said device, said pulse splitting into two pulses which porpagate bi-directionally and circularly around said axis in said test object;

receiving both splitted pulses once per circulation of each of the splitted pulses around the test object, so that a plurality of pulses appear in a receiver portion of said device in the test cycle, the amplitude of the splitted pulses gradually declining;

providing a sequence of burst signals, each of limited duration, as reference signals for purposes of timing and gating, the bursts being repeated per said circulation on the basis of the expected propagation time between transmission and receiving portions providing peak detection of received splitted signals within limited periods of time, per circulation, in synchronism with said reference signals;

digitizing the detected peak signals; and processing said digitized peak signals by forming the quotient of two sets of sequential peak signals in a test cycle.

2. Method as in claim 1 and including the step of forming a first sum of several earlier occurring peaks as digitized, a second sum of several subsequently occuring peaks as digitized and forming the quotient of the two sums.

* * * * *